United States Patent [19]
Arp

[11] 3,934,982

[45] Jan. 27, 1976

[54] BLOOD OXYGENATOR

[76] Inventor: Leon J. Arp, 1107 Highland Circle S.E., Blacksburg, Va. 24061

[22] Filed: May 21, 1974

[21] Appl. No.: 471,876

Related U.S. Application Data

[63] Continuation-in-part of Ser. No. 258,817, June 1, 1972, abandoned.

[52] U.S. Cl. .......... 23/258.5 M; 55/158; 128/DIG. 3
[51] Int. Cl.² .......................................... A61M 1/03
[58] Field of Search ...... 23/258.5, 288 M, 258.5 M, 23/258.5 MH; 261/DIG. 28; 128/DIG. 3; 55/158

[56] References Cited
UNITED STATES PATENTS

| | | | |
|---|---|---|---|
| 1,917,718 | 7/1933 | Jewett | 23/288 M |
| 2,260,152 | 10/1941 | Nelly et al. | 23/288 M X |
| 2,934,067 | 4/1960 | Calvin | 23/258.5 |
| 2,972,349 | 2/1961 | DeWall | 23/258.5 |
| 3,015,331 | 1/1962 | Warrick | 23/258.5 |
| 3,183,908 | 5/1965 | Collins et al. | 23/258.5 |
| 3,247,279 | 4/1966 | Lidov | 23/288 M X |
| 3,332,746 | 7/1967 | Claff et al. | 23/258.5 |
| 3,373,876 | 3/1968 | Stewart | 23/258.5 X |
| 3,441,479 | 4/1969 | Jankay | 23/258.5 X |
| 3,503,850 | 3/1970 | Dibelius | 23/258.5 X |
| 3,506,406 | 4/1970 | Birch | 23/258.5 |
| 3,515,640 | 6/1970 | Rudlin | 23/258.5 X |
| 3,518,033 | 6/1970 | Anderson | 23/258.5 X |
| 3,526,481 | 9/1970 | Rubricius | 23/258.5 |
| 3,579,810 | 5/1971 | Mon | 23/258.5 X |
| 3,612,281 | 10/1971 | Leonard | 23/258.5 X |
| 3,674,440 | 7/1972 | Kitrilakes | 23/258.5 |
| 3,729,377 | 4/1973 | Leonard | 23/258.5 X |
| 3,856,475 | 12/1974 | Marx | 23/258.5 MH |

OTHER PUBLICATIONS

Bodell et al., "A Capillary Membrane Oxygenator;" J. Thoracic Surgery; Vol. 46, No. 5, 11/63; pp. 639–650.
Drake et al.; "The Effect of . . . Circulation;" J. Thoracic & Cardiovasc. Surgery; Vol. 42, No. 6; 12/61; pp. 735–742.
Holt et al.; "Autogenous Oxygenation . . . Clamp;" J. Thoracic & Cardiovasc. Surgery; Vol. 40; No. 4; 10/60; pp. 536–548.
Ratan et al.; J. Thoracic & Cardiovasc. Surgery; Vol. 53, No. 4; 4/67; pp. 520–526.

*Primary Examiner*—Barry S. Richman
*Attorney, Agent, or Firm*—Henderson & Strom

[57] ABSTRACT

A blood oxygenator comprising a first embodiment of a fluid tight housing having a chamber formed therein one end of which is fluid connected by a conduit to a source of blood to be oxygenated, the other end fluid connected for returning oxygenated blood to the source, a plurality of liquid impermeable, gas permeable tubes extended through the chamber for transferring therethrough oxygen at a pressure higher than the partial pressure of the oxygen in the blood, and one or more membranes forming a sealed cavity in the chamber, with openings formed in the housing for tranferring a fluid, such as oxygen into and out of each cavity, movement of a membrane mixing and pumping the blood flowing through the chamber; a second embodiment wherein baffles are disposed within the chamber no membranes being present, for directing the blood as it flows from the one end to the other end in a continually reversing path with the blood normally flowing normal to the tubes for nonmechanical agitation of the blood; and a third embodiment wherein a plurality of bars are inserted each between the adjacent baffles of the second embodiment for promoting circulating of blood from the center of the flow to the surfaces of the tubes, thus destroying the boundary layer of blood next to the tubes.

9 Claims, 12 Drawing Figures

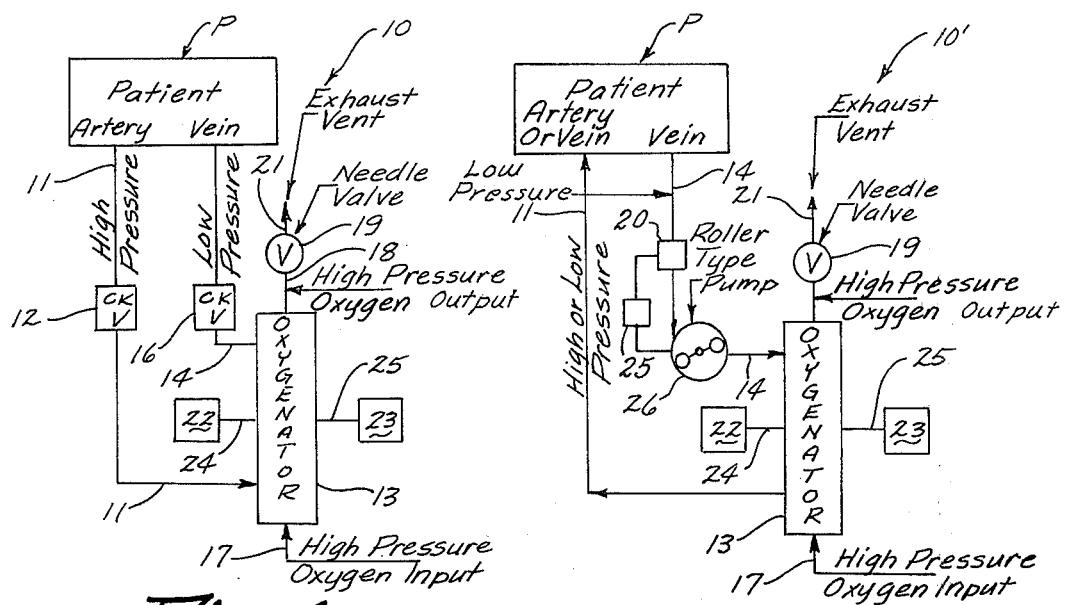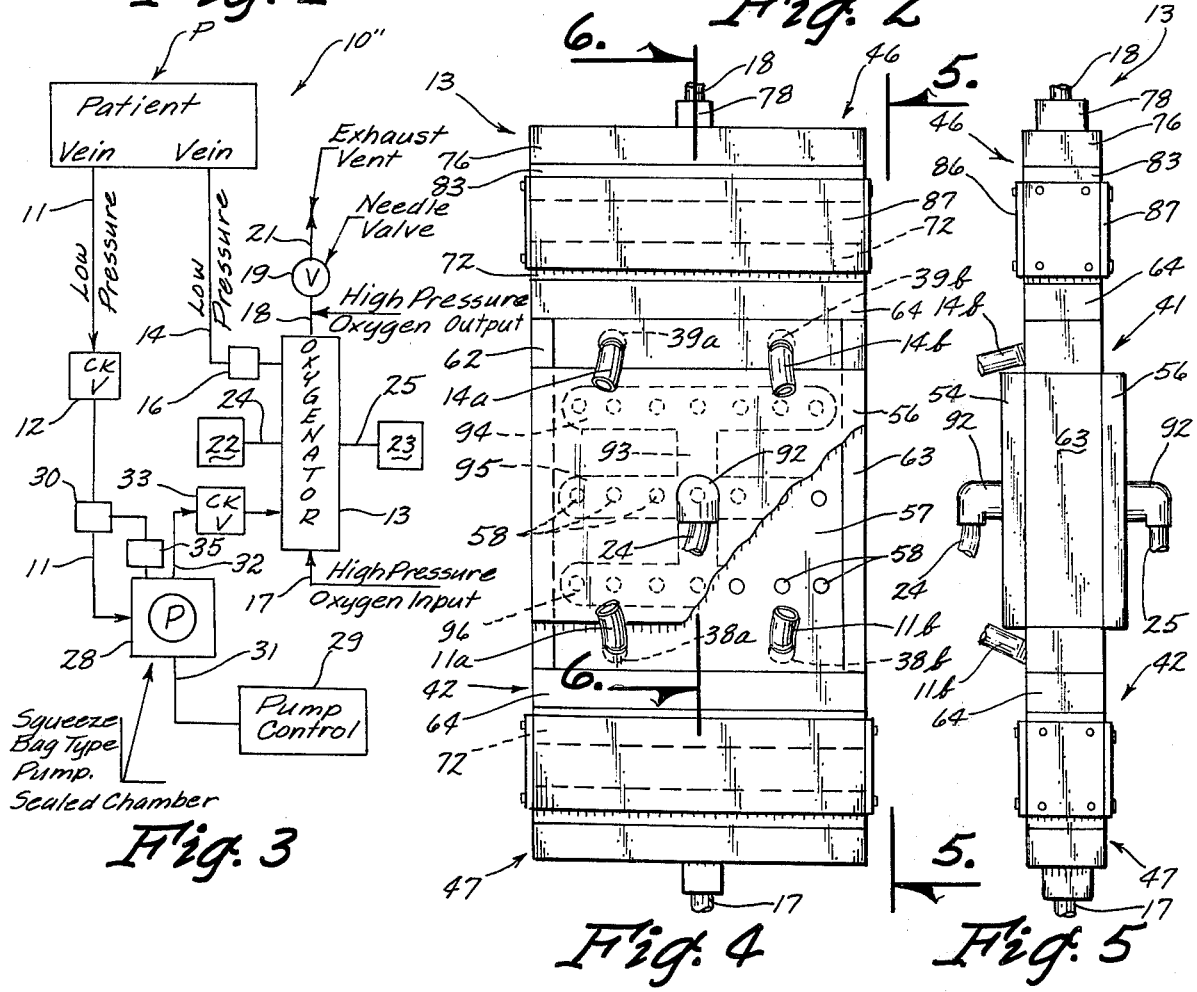

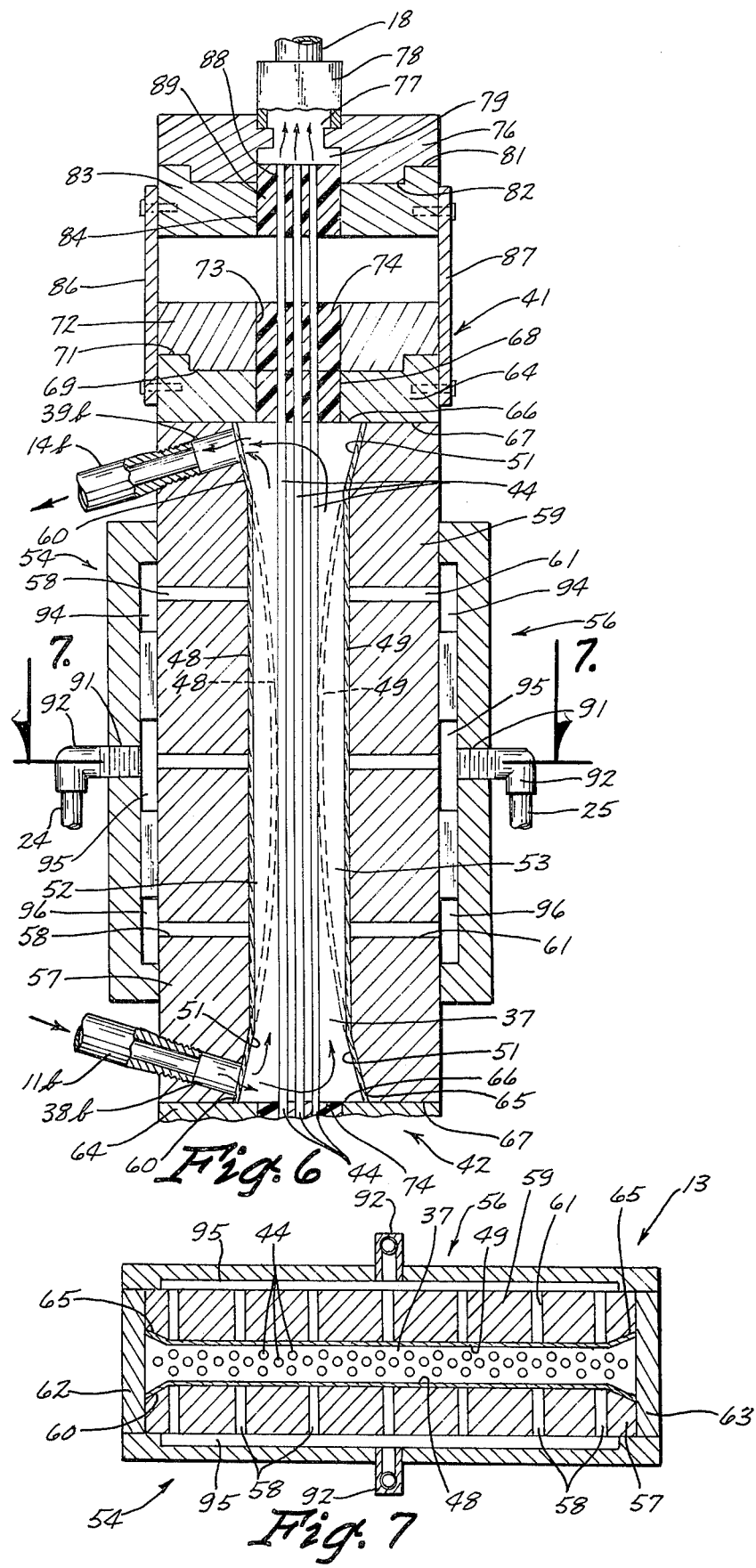

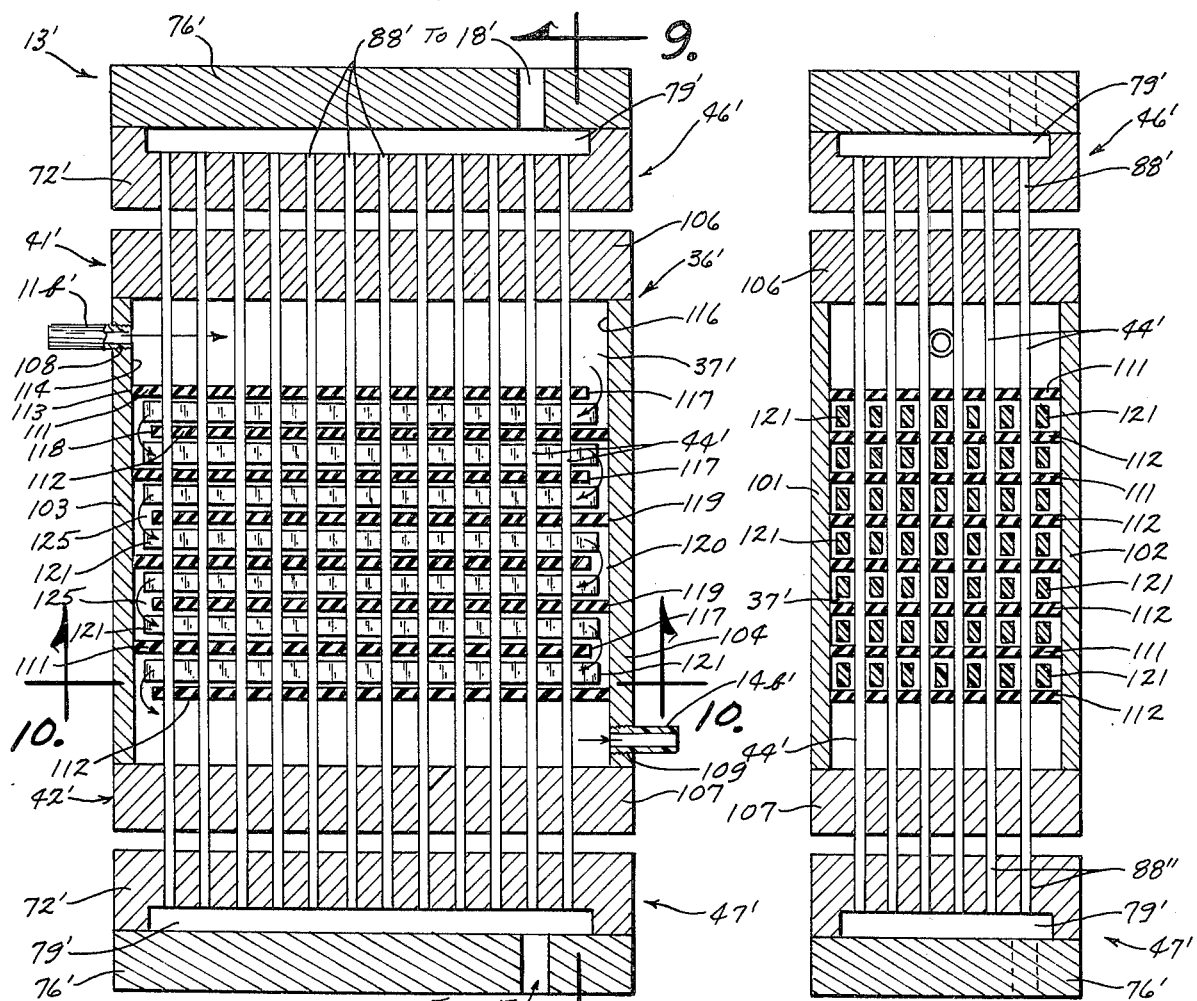
Fig. 8  Fig. 9
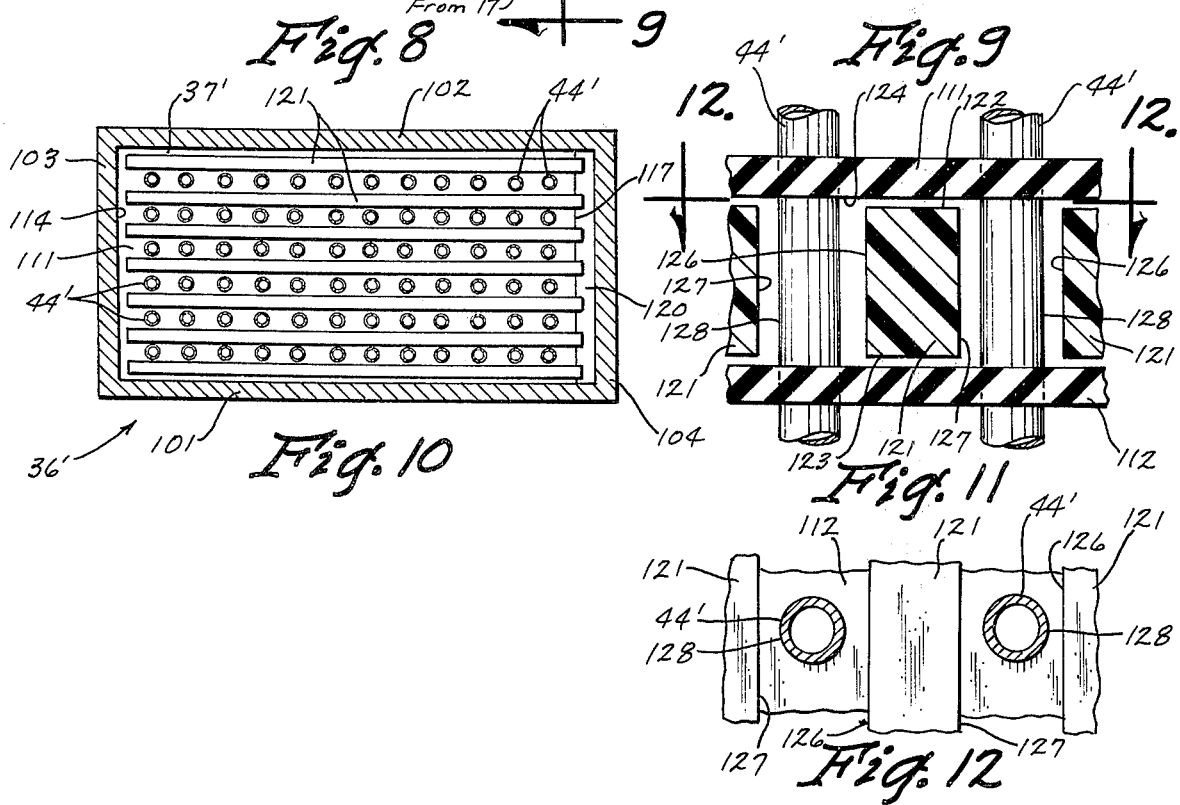
Fig. 10  Fig. 11
Fig. 12

BLOOD OXYGENATOR

This is a continuation-in-part of application Ser. No. 258,817 filed June 1, 1972 for Blood Oxygenator and now abandoned.

BACKGROUND OF THE INVENTION

Natural oxygenation of the blood occurs in the body by the combination of the interaction of the lungs inhaling oxygen at a partial pressure higher than the partial pressure of the oxygen in the blood associated with the lungs, such that molecules of oxygen are transferred across the lung wall, made up of millions of alveoli, and into the blood stream, and with molecules of carbon dioxide passing the opposite direction for discharge from the lungs by exhaling.

Many mechanical, or extra-corporeal blood oxygenators have been tried through the years, as shown in U.S. Pat. Nos. 2,827,901; 3,046,903 and 3,325,641. These and other like devices are unsatisfactory because of damage to the blood. Whether forcing blood under high pressure through a nozzle to be torn into thousands of droplets, or forcing blood through capillary-liketubes about which oxygen is entrained, the shear forces exerted on the red blood cells cause excessive and dangerous hemolysis. Other devices attempt to utilize a large flat surface area in order to obtain adequate gas or fluid transfer through the membrane; however, an increase of the guage pressure of the gas sufficient to obtain satisfactory transfer increases the danger of rupture of the membrane such that the gas, oxygen, is then transferred directly into the bloodstream, a deadly result.

Extracorporeal blood oxygenators may be classified into three major categories: bubble oxygenators, disc oxygenators, and membrane oxygenators. The first two types oxygenate the blood by exposing it directly to the gas phase. This is an efficient method of oxygenation, but due to the direct blood/gas interface, the oxygenators (the bubble more so than the disc) damage the formed elements of the flood and various plasma proteins. In the membrane type oxygenator, a membrane, of which there are various types and designs, separates the blood from the gas phase. The blood damage is reduced significantly, but there are problems involving oxygenation due to the various flow parameters encountered, especially boundary layer phenomenon.

The first bubble type oxygenator was developed in 1950 by L. C. Clarke and his associates. The unit was relatively simple: oxygen was bubbled through a pool of venous blood, and the bubble/blood interface caused the oxygenating surface. This is the most widely used blood oxygenator for cardiopulmonary by-pass despite its high rate of blood damage, since most surgical procedures involving total by-pass rarely require more than an hour to complete.

The disc oxygenator was developed in 1948 by Bjork. This device consists of a series of flat discs which rotate on a central axis and which are surrounded by a chamber containing an ambient gas mixture which flows over and around the upper one-third of the discs; blood is exposed to the bottom two-thirds of the discs. As poorly oxygenated venous blood flows into the chamber, the rotation of the disc forms a thin film of blood on the upper one-third of each disc increasing the blood/gas interface. This process continues for the entire length of the oxygenator. The outlet blood was well oxygenated (approximately 98% saturated), and also, well hemolyzed because of the direct blood/gas interface and high shear forces.

The development of the first membrane blood oxygenator was in 1955 by G. H. A. Clowes, Jr. This oxygenator consists of a series of flat, ultra thin, plastic (ethyl cellulose) membranes which separate the blood phase from the gas phase. The oxygenating capacity of the oxygenator is dependent upon the diffusion of oxygen and carbond dioxide through the membrane. This initial development was followed by various models all operating in the same general manner.

The immediate advantage of the membrane oxygenator was the elimination of the blood/gas interface. Trauma to the formed elements and plasma proteins of the blood was significantly reduced, the oxygenation process being the major problem. A large surface area was needed to oxygenate the blood sufficiently. Consequently, this required many stacks of large, flat membranes that rendered the unit cumbersome. For example, the first oxygenator of Clowes et al was almost 1 foot by 4 feet with a stack of membrane units nearly a foot thick! In addition to the bulkiness of the oxygenator, the membranes were thin and flat, and, therefore, extremely fragile. This became especially hazardous with the development of the fragile silicone rubber membranes. Ruptures were frequent which allowed the formation of gas bubbles in the blood. The large size of most of these units meant large priming volumes, and so they required greater quantities of foreign blood. The major drawbacks, however, were the blood flow geometry, changing blood volumes, and blood mixing.

Membrane oxygenators are divided into two broad and overlapping categories. The first oxygenator type with flat membranes was discussed previously. The second oxygenator type is the capillary membrane oxygenator, in which the membranes are tubular rather than flat. The capillary membrane oxygenator offers several advantages: added strenght due to tubular arrangement and the capability of obtaining a large surface area in a relatively small space. The mode of operation of the capillary membrane oxygenators is the same as that of the flat membrane oxygenators; i.e., oxygen and carbon dioxide diffuse across the membranes at rates proportional to their respective partial pressure gradients.

Capillary membrane oxygenators are further divided into two classes: those with blood flowing through the tubes and oxygen flowing around the tubes, and those with oxygen flowing through the tubes and blood flowing around the tubes.

The vast majority of capillary membrane oxygenators are of the first type. Bodell et al (1963) were apparently the first to use capillary tubing to carry oxygen. They used small diameter silicone capillary tubing (inside diameter 0.012 inches and outside diameter 0.025 inches) of lengths reaching 100 feet. Bodell's model of a capillary membrane oxygenator consisted of a series of repeatable units containing several strands of the tubing wound in a helical loop. The loop formed a lumen through which the blood could flow. Several of these units were assembled in series to form the complete oxygenator. Oxygen transfer was adequate, and hemolysis rates were significantly lower than those of the bubble and disc oxygenators but were still high (66–172mg Hb/100 ml plasma after 90 minutes of continuous oxygenation). In addition, the unit was difficult to assemble, operate, and sterilize.

SUMMARY OF THE INVENTION

The invention comprises an extra-corporeal blood oxygenator of novel construction within a system, for example the oxygenator fluid connected between an artery and one or more veins of a patient with a pump on the low pressure side, or between a pair of veins again with a pump on one side, with appropriate check valves to control the flow of blood through the oxygenator. The oxygenator itself comprises a fluid tight housing having a chamber formed therein opposite ends of which are fluid connected to the patient for transmitting blood under low pressure through the chamber. Within the chamber are a plurality of tubes which pass completely therethrough, and through which oxygen is passed under a pressure higher than the partial pressure of the oxygen in the blood such that oxygenation readily and easily occurs.

The oxygenation process can be made even more efficient and effective by the provision of a membrane sealed to either one or to each of opposite sides of the chamber, and with a plurality of openings formed in the housing inner side covered by the membrane whereby a fluid such as oxygen can be passed into and out of the cavity; thereby, in addition to aiding oxygenation, providing for a mixing and/or pumping of the blood within and through the chamber.

The blood oxygenator of the invention may be used as a total substitute for the lungs during open heart surgery; or it may be used in parallel as a partial bypass of the lungs during surgery, or with newborn infants with poorly functioning lungs. With adults, it could be used in parallel with the lungs for aiding blood oxygenation. A number of these blood oxygenators could be used in series to increase the quantity of oxygen transfer. Furthermore, as will be seen hereinafter, in combination with blood pulsing and pumping controls, it may replace or bypass the heart under certain conditions.

A new extra-corporeal membrane type blood oxygenator and pump has been constructed and tested in vitro by the applicant in the Bio-Medical-Engineering Laboratory at the Virginia Polytechnic Institute and State University at Blacksburg, Virginia. The main objections to oxygenators presently available appear to have been eliminated in this new system. In contrast to the system developed by the Kolobow group at the National Heart Institute, (Kolobow, T. and W. M. Zapol; A Heart-Lung-Placenta Machine ? Roche Medical Image and Commentary, pp. 14–17, October, 1969) one embodiment of the new system has a blood flow path length of only 4½ inches compared to the flow path length of 7 feet for the Kolobow lung. This short flow path eliminates a number of problems found in units requiring longer paths. First, the pressure drop across the device is very small. (Using Bovine blood flowing at 300 milliliters per minute, the pressure drop across the new oxygenator has been measured and found to be 20 mm. Hg., and 10 mm. Hg. at a flow rate of 100 milliliters per minute). These small drops make it possible to use an arterial-venous (A-V) shunt type connection to the patient. Auxiliary ventricle type, pulsatile pumping capability is also provided with the new system if it should be required.

A priming volume of 40 cc. is required for the new oxygenator compared to the 70 cc. required by the Kolobow lung. The small priming volume further improves the potential for successful application with the newborn infant and may eliminate the need for donor blood for priming.

The very small membrane surface area in contact with the blood (0.077 sq.M.) compared to the 0.4 sq.M. of membrane surface area in the Kolobow lung, along with the very short 4½ inch flow path length greatly reduces the trauma to the blood and the tendency for precipitates to form on the surfaces of the membranes. The entire blood circuit, with the exception of the catheters used to cannulate the vessels, is made of silicone rubber, thereby providing maximum protection for the blood flowing through the extra-corporeal circuit.

The membrane material used in the new oxygenator does not require structural reenforcement with nylon knit or mesh, etc. The silicon rubber membrane is 0.011 inch thick compared to the very fragile 0.001 inch material generally used today. Chances for leakage of either blood or gas are obviously greatly reduced by use of the very thick membrane. In addition, fabrication cost is much less when the membrane does not have to be supported or reenforced.

The final measurement of an oxygenator suitable for the specific application described in the introduction to this proposal is the ability of its membranes to transfer oxygen. Dr. Kolobow and his group from the National Heart Institute claim that their oxygenator ". . . has twice the gas transfer efficiency — per sq.M. of membrane — of commerically available membrane oxygenators . . . ". The oxygen transfer rate given by the Kolobow group for their oxygenator is 50 cc per minute per square meter of membrane. The new oxygenator tested in vitro has a measured oxygen transfer of 202 cc of oxygen per minute per square meter of membrane (See FIG. 1). The new oxygenator with its greater oxygen transfer capability (more than four times the transfer rate provided by the Kolobow lung) appears to be a major advance in this field.

The primary purpose of this new oxygenator is to provide sustaining oxygen for the patient in respiratory distress. In the case of the newborn where fetal shunting has reduced the flow of blood through the lungs to an extent incompatible with life, the new oxygenator may be able to increase blood oxygen tension to a level sufficiently high to cause dilation of the pulmonary vessels and partial closure of the ductus arteriosus. This in turn would reestablish an adequate flow of blood through the lungs and provide time for normal restoration processes to take place. The adequacy of oxygen transfer across the new membrane oxygenator has been clearly established. In the past it has been consistently reported that it has not been possible to obtain 100 percent oxygen saturation of blood at required flow rates when the in-flowing blood was poorly saturated (below 30 percent). This can now be accomplished with the new blood oxygenator.

It is an object of this invention to provide a new and novel blood oxygenator system, including a new and novel blood oxygenator as a part thereof.

It is another object of this invention to provide a blood oxygenator system wherein blood at normal pressure is oxygenated by oxygen at a higher pressure than the oxygen partial pressure of the blood in the blood stream.

Still another object of this invention is to provide an extra-corporeal blood oxygenator wherein the shear forces on the blood are at a minimum, and wherein the pressure drop of blood across the oxygenator is very low, all compared to contemporary oxygenators.

Yet another object of this invention is the provision of a blood oxygenator wherein oxygen under a high pressure is passed through a plurality of liquid impermeable tubes about which the blood to be oxygenated flows freely and under a lower partial pressure.

Another object of this invention is to provide a blood oxygenator which is capable of transferring more oxygen per unit area of membranes when compared to contemporary oxygenators.

Still another object of this invention is to provide a blood oxygenator which requires a minimum volume of blood to completely prime the system.

Yet another object of this invention is to provide a membranetype blood oxygenator wherein non-mechanical agitation of the blood is provided by directing the blood continually at right angles to the flow of oxygen while obstructing the center of the blood flow steream to achieve a continual turbulence adjacent the oxygen carrying tubes, thus substantially destroying any boundary layer formation.

Another object is to provide an apparatus capable of attaining the above designated objectives which is economical, effective and efficient.

These objects and other features and advantages of this invention will become readily apparent upon reference to the following description when taken in conjunction with the accompanying drawings.

BRIEF DESCRIPTION OF THE DRAWINGS

FIG. 1 is a schematic of one blood oxygenation system of this invention;

FIG. 2 is a schematic of a second blood oxygenation system of this invention;

FIG. 3 is a schematic of a third blood oxygenation system of this invention;

FIG. 4 is a front elevational view of the blood oxygenator housing unit for the inventions of FIGS. 1 – 3 inclusive, certain parts broken away for clarity of invention;

FIG. 5 is an end elevational view as seen along the lines 5—5 in FIG. 4;

FIG. 6 is an enlarged, fragmentary sectional view as taken along the lines 6—6 in FIG. 4, with broken lines being used for clarity of invention;

FIG. 7 is a reduced horizontal sectional view taken along the lines 7—7 in FIG. 6;

FIG. 8 is an internal view of a modified blood oxygenator, a side wall having been removed;

FIG. 9 is a cross-sectional view of the modification as seen along the line 9—9 in FIG. 8;

FIG. 10 is a sectional view taken along the line 10—10 in FIG. 8;

FIG. 11 is an enlarged detail of FIG. 9; and

FIG. 12 is a sectional view taken along the line 12—12 in FIG. 11.

DESCRIPTION OF THE PREFERRED EMBODIMENT

Referring particularly to FIG. 1, the first blood oxygenator system is indicated generally at 10, and comprises a first conduit 11 fluid connected by a catheter (not shown) or the like to a blood vessel, such as an artery, of a patient P. A one-way check valve 12 may be interposed in the conduit 11 to prevent a reverse flow of blood if necessary, and the other end of the conduit 11 is fluid connected to one end of an extra-corporeal blood oxygenator indicated generally at 13 and described more in detail hereinafter.

Oxygenated blood leaves the oxygenator 13 through a second conduit 14 at a slightly lower pressure, due to a pressure drop across the oxygenator 13, passes through a second optional check valve 16 which permits flow only outwardly from the oxygenator 13, and from thence back to the patient P, the latter acting as a source of blood to be oxygenated.

Oxygen under a pressure higher than the partial pressure of the oxygen in the blood flowing between the conduits 11 and 14 and through the oxygenator 13 is transmitted through an input line 17 into the blood oxygenator for entrainment through a plurality of tubes (See FIG. 6) about which the blood flows, and then outwardly therefrom through an output line 18. A needle valve 19 is interposed in the output line 18 for providing a controlled flow of the oxygen, if necessary, through and outwardly of the tubes, an exhaust vent 21 being provided for the exhausting oxygen and carbon dioxide.

It will be understood that a build-up of carbon dioxide will take place in the oxygen tubes, which gas must be purged from time to time to maintain the effectiveness of the carbon dioxide removal system. The flow and exhaust arrangement of FIG. 1 is one method of dissipating the carbon dioxide.

As will be described in detail hereinafter, mixing and/or pumping of the blood as it flows through the oxygenator 13 is effected by control devices 22 and/or 23 shown in schematic form and fluid connected by conduits 24 and 25 to the oxygenator 13.

In FIG. 2 a second blood oxygenator system is shown, indicated generally at 10', and wherein like parts with the FIG. 1 system 10 are shown by like reference numerals and perform like functions. A roller-type pump 26 is interposed in the second conduit 14 for taking the low pessure blood flow from the patient P and forcing it through the blood oxygenator 13 in a direction reverse to the FIG. 1 system. A collapsible sac or reservoir 20 for blood is added between the pump 26 and the patient, and connected to a control box 26 inserted between the sac 20 and the pump 26. The control box 25 senses the amount of fullness or quantity of blood in the sac 20 and should the pump 26 deliver a greater quantity of blood than is flowing from the patient, such as to cause the sac 20 to begin to collapse, the control 25 would temporarily shut down the pump 26. Practical utilization of the systems will be detailed hereinafter.

A third system 10'' is shown in FIG. 3, again where like parts with the FIG. 1 system are indicated by like reference numerals and perform like functions. A squeeze bag-type pump 28, fluid connected to a control 29 by a line 31, is interposed in the input conduit 11 for pulsing blood through the oxygenator 13 in the same manner as the heart, a conduit 32 and check valve 33 therein being provided between the pump 28 and the blood oxygenator. The check valve 33 is provided to prevent the flow of blood from the oxygen back through conduits 32 and 11 to the patient P. Again, a collapsible sac or reservoir 30 for blood is added between the pump 28 and the patient, and connected to a control box 35 inserted between the sac 30 and the pump 28. The control box 35 senses the amount of fullness or quantity of blood in the sac 30 and should the pump 28 deliver a greater quantity of blood than is flowing from the patient, such as to cause the sac 30 to begin to collapse, the control 35 would temporarily shut down the pump 28.

Referring particularly to FIGS. 4–7 inclusive, the extra-corporeal blood oxygenator 13 is illustrated. Generally, the oxygenator comprises a housing unit 36 having a fluid tight chamber 37 formed therein at one end of which a pair of inlet openings 38a and 38b are formed for connection the Y ends 11a and 11b of conduit 11, for receiving blood therefrom for example, and at the other end of which a pair of outlet openings 39a and 39b are formed for connection to the Y ends 14a and 14b of conduit 14, for transferring blood thereto for example, The chamber 37 is sealed at the upper end by a sealing device 41 and at the lower end by a like sealing device 42.

For transmitting oxygen under pressure through the blood chamber 37, a plurality of parallel tubes 44 running the length of the chamber 37 are secured within the chamber 37 so as to be surrounded by the blood therein. The tubes 44 pass through the chamber sealing devices 41 and 42 and are themselves sealed at their upper and lower ends by like sealing devices 46 and 47 (FIG. 5).

Mounted within the chamber 37 are a pair of thin, flexible diaphragms 48 and 49 of fluid impermeable material, each cemented about its periphery 51 to the inner perimeter side wall surface defining the chamber 37. Openings (now shown) are formed in the diaphragm 48 on the housing side where the blood inlet and outlet openings 38 and 39 are found, for passing blood therethrough, however these do not effect the formation of a pair of expandable cavities 52 and 53 between the respective diaphragms 48 and 49, respectively, and the adjacent housing wall. In FIG. 6, by the use of dotted lines showing inward movement of the diaphragms 48 and 49, the cavities 52 and 53 are clearly illustrated. This movement agitates and may even pump the blood within the chamber 37 as described hereinafter.

For the purpose of passing a fluid, such as oxygen into and out of the cavities 52 and 53, a pair of manifold units 54 and 56 are provided, unit 54 connected by conduit 24 to control device 22, and unit 56 connected by conduit 25 to control device 23.

More particularly, the housing unit 36 comprises a face piece 57 (FIG. 6) having a plurality of openings 58 formed centrally therein for the manifold unit 54, in addition to the blood inlet and outlet openings 38a and 38b, 39a and 39b; a rear piece 59 also having openings 61 formed therein and which is identical to the front piece 57 except for not having the blood openings; and a pair of end pieces 62 and 63 (FIG. 4) for completely enclosing the chamber 37 along with the upper and lower chamber seal devices 41 and 42. The inner perimeters of the front and rear pieces 57 and 59 are cut away slightly at 60 and 65 as illustrated in FIGS. 6 and 7 to form a peripheral sealing surface for the diaphrams 48 and 49 as described hereinbefore.

The top and bottom chamber seal devices 41 and 42 are identical and only one will be described, with like parts indicated by like reference numerals. Referring to FIG. 6, the top device 41 comprises an inner element 64 having an inner surface 66 which fits flush in a fluid tight manner with mating surfaces 67 on the front and rear pieces 57 and 59 and also with mating upper surfaces (not shown) on the end pieces 62 and 63. The inner element 64 also has an elongated opening 68 which extends across the width of the housing 36 and which is disposed centrally of the thickness as best illustrated in FIG. 6.

A cut-out outer surface 69 is also formed on the element 64 to accommodate a mating surface 71 of the outer element 72. The outer element 72 also has an opening 73 identical to the inner element opening 68. The elements 64 and 72 are sealed to each other and to the face piece 57, the rear piece 59 and the ends 62 and 63 by silicone rubber cement, epoxy or the like; and with the tubes 44 extended through the openings 68 and 73, a fluid epoxy 74 or the like is poured therein and then allowed to set, closing off the chamber 37 from the atmosphere, except for the blood and manifold openings. By this arrangement, gas leakage into the oxygenator chamber 37 is prevented.

The top and bottom tube seal devices 46 and 47 are also identical and only one will be described, like parts indicated by like reference numerals. Referring to FIG. 6, the top device 46 comprises an outer element 76 which has a centrally located, circular upper opening 77 for accommodation of a fluid fitting 78 for a conduit 18, and with an elongated lower opening 79 which extends across the width of the housing to accommodate all of the oxygen tubes 44. The bottom surface 81 of the outer element 76 fits into a mating cut-out surface 82 of an inner element 83, which also has an elongated tube-embracing opening 84 formed therein.

It will be noted that the elements 76 and 83 of the top seal device 46 have the same length and width as the elements 64 and 72 of the chamber top seal device 41, whereby the two devices 46 and 41 can readily be attached in spaced relation by brackets 86 and 87. Again, with the upper ends 88 (FIG. 6) of the tubes 44 held in the lower opening 79, a fluid epoxy 89 is poured into the opening 84 and partially into the opening 79, then allowed to set to thereby seal the tubes 44 in the openings. The elements 76 and 83 are also sealed together by a silicone rubber cement or the like.

The space enclosed by the brackets 86 and 87, of which there are only two, is open to the atmosphere. Thus, should there by any leakage of the high pressure oxygen from either upper or lower chambers 77 along the tubes 44, rather than harmfully leaking into the blood chamber 37 the oxygen escapes harmlessly into the atmosphere.

The manifold units 54 and 56 are identical, with each having a central opening 91 for receiving a fluid fitting 92 for the respective control device conduit, and with a vertical groove 93 (FIGS. 4 and 6) branching off into a trio of horizontal grooves 94, 95 and 96 for carrying a fluid to the housing openings 58 and 61.

An example of the size of one embodiment actually built and tested has the width or face of the outer elements 76 and 72 as 4-7/16 inches with a depth of 1-1/16 inches and a thickness of ¼ inch. The other top and bottom seal device elements are of comparable sizes as illustrated. The depth, front to rear, of the chamber 37 as seen in FIG. 6, is approximately five-sixteenths inch, and the height is 4-⅝ inches. Approximately 21 of the holes 58 and the same number for 61 are formed in the three rows in the front and rear pieces 57 and 59.

The tubes 44 are of a fluid impermeable silicone rubber having a total surface area in contact with the blood of approximately 120 sq. inches. The number of tubes 44 depends upon the rate of oxygenation required, and with each tube having an outside diameter of .047 inch and an inside diameter of .025 inch. A medical grade tubing sold by Dow Corning Corporation under the trademark Silastic has been used with success. Silastic is physiologically inert, will not support bacterial or common fungal growth, and is a non-wetting silicone elastomer surface.

The diaphragms 48 and 49 (FIG. 6) are a thin membrane of silicone rubber either permeable to the flow of a fluid such as oxygen therethrough, or not, depending upon the system and the use of the blood oxygenator 13.

The system 10 of FIG. 1 assumes that the arterial blood pressure is high enough to force blood through the oxygenator 13 and back to the patient P at a high enough flow rate to meet the patient's oxygen requirements. The system of 10' in FIG. 2 assumes that the pressure of blood in conduit 14 leading to the oxygenator 13 is at an equal or lower pressure than the output conduit 11, thereby requiring the pump 26 to obtain the necessary blood flow through the oxygenator 13. The system 10'' in FIG. 3 assumes that the pressure in conduits 11 and 14 are nearly equal, the squeeze bag-type pump 28 interposed in conduit 11 to obtain the desired blood flow through the oxygenator 13.

Turning now to the function of the membranes 48 and 49 (FIGS. 6 and 7), they are not necessary for any of the systems 10, 10' or 10'' to function; however their presence would improve the function of any of the three systems. It is known that the blood immediately adjacent the exterior surface of the tubes 44 has a high partial pressure of oxygen which reduces the quantity of oxygen transferred across the wall of a tube 44. This is because the rate of oxygen transfer across the wall of a tube 44 is directly proportional to the difference in partial pressure of oxygen on the inside of the tube 44 and on the outside thereof.

It has been found that agitation of the blood in the chamber 37 and about the tubes 44 will disturb the said boundary of oxygen rich layers. Therefore, by alternately inflating and deflating the cavities 52 and 53, the membranes 48 and 49 are moved back and forth within the chamber 37, thereby agitating and disturbing the blood, and aiding the oxygenation. The membranes 48 and 49 can be non-permeable; or if permeable, oxygen can be used as the movement fluid, such that additional surface is provided for increased oxygenation.

Referring to the system 10'' of FIG. 3, assuming the cavities 52 and 53 are inflated simultaneously such that the membranes 48 and 49 are moved inwardly of the chamber 37 simultaneously, with the check valves 33 and 16 working as described hereinbefore, blood is pumped out of the oxygenator 13 through check valve 16 and conduit 14 to the patient P. Continued and regularly applied alternate deflation and inflation of the cavities 52 and 53 results in regular pumping outwardly of the blood from the oxygenator and sucking inwardly of blood thereto from the conduit 32. The pump 28 could then be eliminated.

Utilizing the system 10 as a basis, following is an example of a use thereof. To prime the system, 40 ml of blood is necessary. The priming blood should be at least 12 hours fresh for best results, it having been ascertained from actual testing that 72 hour old blood is extremely difficult to oxygenate. Saline, glucose or lactate ringer solution may alternately be used for priming the system.

With a flow path length of the tubes 44 of 4½ inches in the oxygenator 13, a surface area of 0.077 sq.M. of tube wall contact with the blood, a tube wall thickenss of 0.011 inches, and a blood flow rate of 300 ml/minute, the result is that an input oxygen partial pressure of 20 mm Hg is increased to 150 mm Hg, with there being but a 15–20 mm Hg pressure drop of the blood across the oxygenator 13. With a theoretical maximum limit of oxygen transfer across a .005 inch thick silicone rubber membrane being 238 ml of oxygen per minute per square meter (Secondary Flow and Mass Transfer in an Oscillating Torus, Mechanical Devices for Cardiopulmonary Assistance, Advances in Cardiology, Vol. 6, pp. 40–55 (Karger, Basal 1971)), if 30 psig is applied to the interior of the oxygen transfer tubes 44, even with their having a wall thickenss of .011 inches the transfer is 202 ml of oxygen per minute per square meter. It can be extrapolated that with a tube 44 wall thickenss of .005 inches, the oxygen transfer within the oxygenator could quite possibly be four times the 202 ml transfer, or over 800 ml per minute per square meter.

When membrane oxygenators were first introduced, their most significant advantage over the direct contact units was the alleviation of much of the associated trauma to the formed elements of the blood. However, effective oxygenation of the blood was much less in the membrane oxygenator. It is well documented in the literature that the major hinderance to the transport of oxygen lies not in the membrane itself, but in the blood film geometry. In most membrane oxygenators, the blood flow is laminar; i.e., not turbulent. As with any flowing fluid, blood follows the rules of fluid mechanics. At any given longitudinal section of an oxygenator perpendicular to the blood flow, the velocity distribution usually follows a parabolic flow pattern; this is because blood in a steady state, laminar flow behaves like a homogenous, non-Newtonian fluid. The maximum velocity is at the center of the flow and is approximately twice the average velocity. This flow pattern results from frictional effects of the membrane surface of the blood. In essence, there is a slower moving layer of blood of finite thickness, the boundary layer, next to the membrane surface. There is near zero flow in the region of the membrane, and this results in a diffusion controlled mass transfer which is definitely more significant in dictating the physical dimensions of an oxygenator than any other factor. Therefore, greater membrane surface areas are required resulting in large, cumbersome units. This in turn requires larger priming volumes and may cause an increase in blood trauma.

The boundary layer is of concern to the development of membrane oxygenators. The effective diffusion of oxygen through the blood depends on an oxygen partial pressure ($pO_2$) gradient; this is, of course, the operative method of the lungs. Diffusion is from an area of high partial pressure (oxygen side of the membrane) to an area of low partial pressure (the blood). If any area in this process becomes oxygen saturated, the $pO_2$ gradient slows down or completely stops. This is what happens with a boundary layer formation. The plasma and red blood cells adjacent to the membrane are rapidly saturated with oxygen. Also, the diffusability of oxygen through the plasma itself is slow compared to its diffusability through the membrane. The combination of these two events destroys the $pO_2$ gradient, thus slowing down or stopping the flow of oxygen into the center of the blood flow. Any additional oxygen moving into the boundary layer serves only to increase the saturation of the hemoglobin in this region and may cause the formation of free gas bubbles in the blood. This is especially true for oxygenators that operate with a high $pO_2$ on the gas side of the membrane such as the present oxygenator.

To achieve maximum oxygen transfer, the modified oxygenator 13' of FIGS. 8 – 12 inclusive was developed and tested successfully. In describing it, all parts like or nearly like those of the oxygenator 13 are indicated by like reference numerals plus a prime, and will not be described in detail.

The modified oxygenator 13' does not have the diaphragms 48, 49 which form expandable cavities 52, 53, nor the manifold units 54, 56, nor the face pieces 57, 59 with openings formed therein, all for enabling fluidic forced agitation of the blood in the chamber 37.

The modified oxygenator 13' does however include an air-tight housing 36' having front 101, rear 102, and end walls 103 and 104 joined by top and bottom elements 106 and 107, and a chamber 37' formed therein. The chamber 37' has an inlet 108 (FIG. 8) formed at an upper end 103 which is connected to the end 11b' of the system 10', for example, of FIG. 3, and has an outlet 109 formed at a lower end 104 which is connected to the end 14b' of the FIG. 3 system. Operation of the system 10'' described hereinbefore, without the use of the control devices 22 and 23 as was explained, and using a ventricle-type pump 28' would effect a pulsating flow of blood having oxygen therein at a certain partial pressure through the inlet 108, the chamber 37', and out the outlet 109.

To direct the flow of the blood in the chamber in a certain path, a baffle system including a first set of baffles 111 (FIGS. 8 and 9) and a second set of baffles 112 is mounted within the chamber 37. Each baffle 111 and 112 has a width equal to the inner spacing of the front and rear walls 101 and 102 (FIG. 10), and a length not quite equal to the inner distance between the end walls 103 and 104. The first set of baffles 111 are mounted in spaced relation with common ends 113 (FIG. 8) abutting the inner surface of wall 114 which is opposite and parallel to wall 116. The other ends 117 of the first set of baffles 111 are spaced from the surface 117 of the opposite wall 116 whereby a space 120 is formed therebetween.

The common ends 118 of the second set of baffles 112 are spaced from the surface of the wall 114, with the opposite ends 119 abutting the wall 116 such that a space 125 is formed between each end 118 of the baffles 112 and the adjacent wall surface 114.

By placing the baffles 111 and 112 in the alternating arrangement as best illustrated in FIGS. 8 and 9, and in view of the alternating spaces 120 and 125 as shown in FIG. 8, the blood is directed in a continually reversing path as is shown by the arrows in FIG. 8 from the inlet 108 to the outlet 109, which path is normal to the disposition of the tubes 44' within the chamber 37', the tubes 44' being parallel to the surfaces 114 and 116 of the opposite walls 103 and 104. It is seen furthermore by this arrangement that the blood is channeled through the oxygenator without mechanical agitation effected by moving parts of the oxygenator 13' while still being able to disrupt the boundary layer adjacent the tubes 44'.

Instead of the blood flow being parallel to the tubes 44', as is seen in the illustrations, the flow of blood between the walls 103 and 104 is mostly perpendicular to the tubes 44'. This pattern causes a gentle mixing of the blood destroying much of the boundary layer. Tests as to hemolysis results indicated no significant blood damage, excluding sublethal damage which was not determined.

To further enhance destruction of the blood layer formation, blood flow obstruction means were added to the modified oxygenator 13'. These comprised a plurality of elongated bars 121 of Teflon or like material. Each bar 121 is inserted, as is clearly illustrated in FIGS. 8 – 12 inclusive, between adjacent pair of baffles 111 and 112, and adjacent pairs of tubes 44'. The dimensions of the bars 121 are best shown in FIGS. 11 and 12, wherein the upper and lower surfaces 122 and 123 of each bar are closely adjacent the surfaces 124 of adjacent baffles 111 and 112. Furthermore, the thickness of each bar 121 is such that the side surfaces 126 and 127 thereof are closely adjacent the peripheral surfaces 128 of adjacent pairs of baffles 44'. Each bar 121 has one or more projections on the surfaces 122 and 123 which would engage the adjacent surfaces 124 for securement therebetween.

By this provision, it can readily be appreciated, particularly from FIG. 8, that as blood flows around the end 117 of baffle 111 so as to flow from right to left as one views FIG. 8, toward the wall surface 114, the provision of the bar 121 between the lower surface 124 of the baffle 111 and the upper surface 124 of the baffle 112, forces the blood to flow in a turbulent manner past the tubes 44' at that position in the chamber 37'. Furthermore, the obstruction to the flow of blood due to the bars 121 of course increases the velocity of flow adjacent the tube surfaces, which when added to the increased turbulence, further tends to destroy the layer foundation along the surfaces of the tubes 44'.

It is to be noted that as with the FIG. 3 system 10'', oxygen under a pressure higher than the partial pressure of the oxygen in the blood flowing in the chamber 37' is continually transmitted during operation of the oxygenator 13' through the input line 17' into the tubes 44' for transmission therethrough and to the output line 18'.

I claim:
1. An extra-corporeal blood oxygenator comprising:
   a housing forming an oxygenation chamber; blood inlet means at one end of said chamber for passing blood, at a certain pressure, to be oxygenated into said oxygenating chamber, and blood outlet means at the other end of said chamber through which the oxygenated blood is discharged; and
   a plurality of tubular elements of a liquid impermeable, gas permeable material extending through said oxygenating chamber and in contact therein with said blood as the blood passes through said chamber; oxygen inlet and outlet means located at opposite ends of said tubular elements for carrying oxygen therethrough at a partial pressure greater than the partial pressure of the oxygen in the blood as the blood is transmitted through said chamber; and wherein said oxygenating chamber has a pair of opposed sidewalls, said oxygenator further including a pair of opposed flexible walls located within said oxygenating chamber, each said flexible wall being sealed about its periphery to one of said opposed sidewalls of said chamber, and means attached to said housing, including a plurality of spaced openings formed in a portion of said housing, for transmitting a fluid through said openings and into a cavity formed between each respective pair of a chamber sidewall and a flexible wall sealed thereto to move said flexible wall within said chamber, said flexible walls being adapted to contact the blood moving through said chamber and operable, upon movement thereof by said fluid, to agitate said blood within said chamber.

2. An extra-corporeal blood oxygenator as defined in claim 1, and wherein said fluid is oxygen at a partial pressure higher than the partial pressure of the oxygen in said chamber, and said flexible wall is constructed of a liquid impermeable material.

3. An extra-corporeal blood oxygenator as defined in claim 1, and wherein said blood inlet means comprises a blood inlet line having a check valve, interposed therein connected to said housing one end for permitting blood to flow only into said chamber, and a blood outlet line having a second check valve interposed therein connected to said housing other end for permitting blood to flow only out of said chamber.

4. An extra-corporeal blood oxygenator comprising:
   housing means having an oxygenating chamber formed therein and having blood ingress and blood egress means for said chamber;
   means connected to said ingress means for transmitting blood in a pulsating manner under pressure to be oxygenated into said chamber;
   tubular means disposed within said chamber and comprised of a liquid impermeable, gas permeable material;
   means connected to said tubular means for transmitting oxygen therethrough under a partial pressure greater than the partial pressure of oxygen in the blood within said oxygenating chamber;
   baffle means mounted within said chamber and including a plurality of spaced baffles, said plurality of baffles being longitudinally spaced apart relative to and located between said blood ingress and blood egress means, alternate ones of said baffles engaging opposite walls of said chamber, said baffle means directing the blood through said chamber in a continually reversing path between said ingress and egress means, said path being substantially normal to said tubular means when disposed between said walls; and
   means connected to said egress means for withdrawing the oxygenated blood from said chamber.

5. An extra-corporeal blood oxygenator as defined in claim 4, and wherein said chamber has a pair of opposed walls extending parallel to each other, and further wherein said tubular means includes a plurality of tubes of liquid impermeable, gas permeable material disposed within said chamber in parallel relation with each other.

6. An extra-corporeal blood oxygenator as defined in claim 5, and wherein said tubes are disposed in parallel relationship with said chamber walls.

7. An extra-corporeal blood oxygenator as defined in claim 6, and wherein said baffle means includes a first set of baffles mounted in spaced relation in said chamber with common first ends abutting one of said pair of opposed walls of said chamber and with common second ends spaced from the other of said pair of opposed walls of said chamber, a second set of baffles mounted in spaced relation in said chamber with common first ends spaced from said one wall and with common second ends abutting said other wall whereby the blood from said ingress means flows in a constantly reversing path within the housing until it passes through said egress means.

8. An extra-corporeal blood oxygenator as defined in claim 7, and further including means disposed between each pair of baffles and each pair of tubes for reducing the space therebetween whereby the flow of blood is obstructed.

9. An extra-corporeal blood oxygenator as defined in claim 8, and further wherein said blood flow obstruction means comprises a plurality of elongated bars, each bar disposed between a pair of adjacent baffles and between a pair of adjacent tubes.

* * * * *